United States Patent [19]
Tobinick

[11] Patent Number: 6,149,645
[45] Date of Patent: *Nov. 21, 2000

[54] APPARATUS AND METHOD EMPLOYING LASERS FOR REMOVAL OF HAIR

[76] Inventor: Edward L. Tobinick, 100 UCLA Medical Plz., Suite 205, Los Angeles, Calif. 90024-6903

[*] Notice: This patent is subject to a terminal disclaimer.

[21] Appl. No.: 09/054,571

[22] Filed: Apr. 3, 1998

[51] Int. Cl.⁷ .................................................. A61B 18/18
[52] U.S. Cl. ................................ 606/9; 606/10; 606/16; 606/19
[58] Field of Search .................................. 606/2, 3, 9, 10, 606/11, 12, 13, 16, 17, 18, 19

[56] References Cited

U.S. PATENT DOCUMENTS

| | | | |
|---|---|---|---|
| 4,791,927 | 12/1988 | Menger | 606/10 |
| 5,150,704 | 9/1992 | Tatebayashi et al. | 606/10 |
| 5,540,676 | 7/1996 | Freiberg | 606/3 |
| 5,658,323 | 8/1997 | Miller | 606/9 |
| 5,662,644 | 9/1997 | Swor | 606/9 |
| 5,785,703 | 7/1998 | Goodman et al. | 606/10 |
| 5,843,072 | 12/1998 | Furumoto et al. | 606/9 |
| 5,873,875 | 2/1999 | Altshuler | 606/10 |

Primary Examiner—Michael Peffley
Assistant Examiner—Bryan Yarnell
Attorney, Agent, or Firm—Ezra Sutton

[57] ABSTRACT

A laser apparatus for permanently removing a plurality of hair follicles or blood vessels from the skin of a patient. The laser apparatus includes a housing having first and second lasers contained therein for emitting at least first and second pulses of coherent light energy; first and second fiber optic bundles connected to the first and second lasers, respectively, for transmitting the pulses of coherent light energy from the first and second lasers; the first and second fiber optic bundles connected to a common fiber optic bundle for combining and transmitting at least first and second pulses of coherent light energy from each of the first and second lasers through the common fiber optic bundle; and a sequence control device for controlling the first and second lasers to emit at least first and second pulses of coherent light energy either sequentially or simultaneously, with a time delay of less than 100 milliseconds between the sequential pulses from the first and second lasers. The laser apparatus further includes a handpiece for holding a section of the common fiber optic bundle in order to direct at least first and second pulses of sequential or simultaneous pulses of coherent light energy from the first and second lasers to a selected spot of the patient's skin to remove a plurality of hair follicles or blood vessels. In an alternate embodiment, other optical delivery systems may be employed, such as an articulated laser arm assembly.

40 Claims, 11 Drawing Sheets

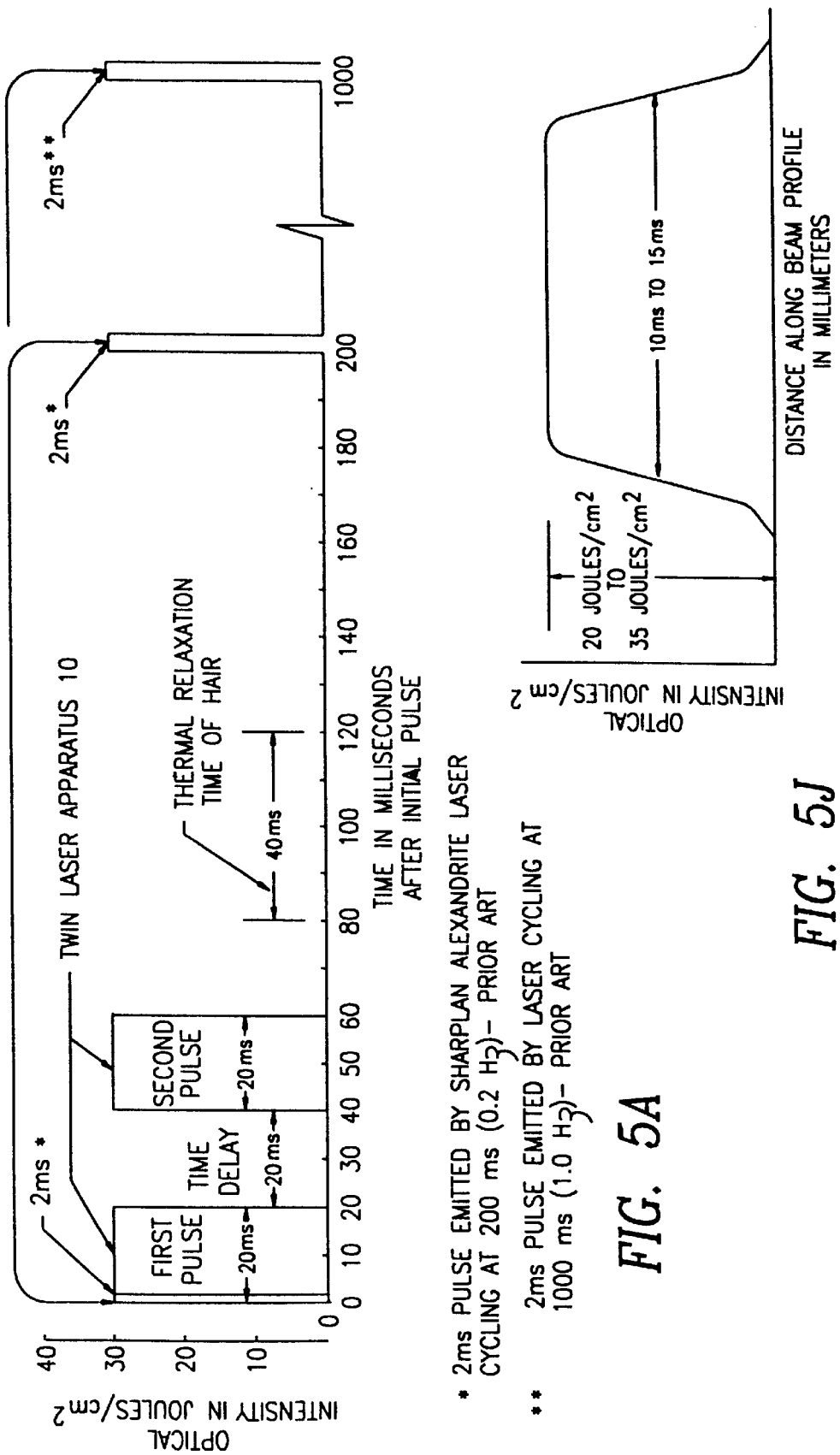

THERMAL RELAXATION TIME: CLINICAL VARIATIONS RELEVANT TO LASER HAIR REMOVAL

APPARATUS AND METHOD EMPLOYING LASERS FOR REMOVAL OF HAIR

An apparatus and method for removing hair from the skin of a patient is provided using a laser apparatus having at least first and second lasers, a sequence control device and an optical delivery system including the steps of controlling the first and second lasers to emit at least first and second pulses of coherent light energy sequentially, transmitting at least first and second pulses of coherent light energy to the same spot on the skin of the patient through a common light transmission pathway, irradiating the same spot on the skin containing the hair with at least first and second sequential pulses of coherent light energy through the common light transmission pathway from the first and second lasers, pulsing one of the first and second lasers at a specific wavelength in nanometers, at a power level in Joules/cm$^2$, a specific pulse duration in milliseconds, a specific pulse delay in milliseconds, and a specific beam diameter on the treatment area in millimeters, and pulsing the other one of the first and second lasers at a specific wavelength in nanometers, at a power level in Joules/cm$^2$, a specific pulse duration in milliseconds, and a specific pulse delay in milliseconds, and a specific beam diameter on the treatment area in millimeters.

FIELD OF THE INVENTION

This invention relates to an improved laser apparatus and method employing two lasers coupled by a sequence control device for removal of hair, or veins or capillaries, and more particularly, it relates to two lasers emitting two or more sequential pulses of light energy, which are transmitted through the same optical delivery system, to the same area of the skin being treated.

BACKGROUND OF THE INVENTION

Hair removal by lasers is a new clinical field developed in the early nineties and only commercially available to patients since 1996. Lasers allow the rapid removal of large areas of hair, veins or capillaries on almost any body area, such as on the face, arms, legs, breasts, hands, stomach and the like. Laser treatment provides an unusually low discomfort level to thee patient, and hair removal may last for weeks on a body area. However, all of the current lasers used for hair removal are problematic and produce unwanted side effects such as burning the skin, changes in skin pigmentation, and sometimes permanent scarring.

The currently available lasers use different approaches to hair removal, and use different laser technologies. For example, the ND:YAG laser was the first commercially available laser, but is the least effective, and does not provide permanent hair removal. The ruby laser emits a fixed wavelength of 694 nm, but has a propensity to burn the skin of the individual being treated. Because of this problem, ruby lasers cannot be used to treat olive-skinned or tanned individuals. The alexandrite laser emits a fixed wavelength of 755 nm (near the infrared spectrum), but has a propensity to burn the skin of the individual being treated, and is less effective than ruby laser treatment. Also, lasers presently being used do not consistently and reliably provide permanent hair removal, they require multiple treatments, and often burn the skin.

Pulsed flashlamps have also been used for hair removal, and they emit filtered visible light having wavelengths in the range of 550 nm and above, but they also have not been effective in providing permanent hair removal.

Current cutaneous lasers work by delivering energy in the form of laser light which is absorbed by the cutaneous target, heating the target and thereby causing its destruction. Different skin structures have different colors, different surface to volume configurations, and other factors which cause differential rates of heat loss. All of the hair removal lasers work by application of the principal of selective photothermoloysis, i.e. selective destruction due to heat caused by absorption of light. Laser light, which has a single wavelength, is optimally absorbed by a target which has a complementary specific color. This laser target is called a chromophore. The usual chromophore for hair removal lasers is melanin, found in high concentration in brown and black hair, and is responsible for the color of hair.

The clinical problem is that melanin is also found in the epidermis, and is responsible for native skin color and tan. Laser energy is therefore also absorbed into the epidermis. The problem of hair removal by lasers therefore is to deliver laser energy that heats the hair to a sufficient degree to cause permanent damage and hair loss, yet spare the skin of any damage. Present lasers are unable to accomplish this. For example, ruby lasers work in removing hair follicles because the wavelength of 694 nm which is emitted, is selectively absorbed by melanin and less so by other cutaneous structures, such as blood vessels. In fair skin, with little melanin, selectivity is sufficient to allow sparing of the skin and destruction of hair with even a single pulse. Alexandrite lasers perform similarly, but since their absorption by melanin is somewhat lower they seem to be less effective than ruby lasers, at least in their current forms.

The Cynosure® laser adds another approach, which they call Thermokinetic Selectivity™. This means the selective destruction of the target with the same chromophore as the skin (i.e. melanin), due to less efficient heat conduction out of the hair (as compared with the epidermis). This less efficient heat conduction is due to a variety of factors, the main one being the unfavorably large volume to surface area of the hair. The Cynosure® laser, like the ruby lasers, uses a single pulse, but the pulse used by this alexandrite laser is longer (5–20 ms). This longer pulse allows more gradual accumulation of heat by the skin, so the heat has time to dissipate (cool) and to prevent burning of the skin. This technique improves safety, but the technique is not able to deliver enough heat to provide permanent hair loss, and some burns still occur.

The use of medical lasers to produce permanent hair removal in patients with hairs of all colors, and skin of all colors, has, up to this time, been impossible to achieve with current technology. While promising, the currently-used lasers have all been unable to treat patients with dark skin. In addition, even in Caucasian patients, the currently-used lasers have burned many patients, leading to prolonged changes in skin color and even, in some cases, to permanent scarring. Hair loss, although usually prolonged, has not been permanent for the majority of patients.

Nevertheless, the use of monochromatic (laser) light in the range of 694 to 900 nm still appears to be the most effective way to achieve long-term hair removal. To achieve predictable permanency, higher temperatures in the hair must be achieved without heating the epidermis to the point where it is burned. The single pulse techniques described above are inadequate to accomplish this.

There remains a need for an improved laser apparatus and method which will supply a high level of laser energy to heat a hair follicle sufficiently to cause permanent damage to that hair follicle and permanent hair removal, and yet spare the skin from burning, thus providing a safe and permanent method of hair removal.

A new laser has been developed that has the following major advantages: 1) increased efficacy, causing greater hair loss and true permanent hair removal; 2) increased safety, with burning of the skin eliminated, so that treatment has no side effects; 3) increased speed of treatment, nearly by a factor of two; and 4) it allows the use of laser hair removal for patients with dark skin, thereby greatly increasing the range of people who can be treated with this technology.

DESCRIPTION OF THE PRIOR ART

Laser apparatus and methods for hair removal having various structures have been disclosed in the prior art. For example, U.S. Pat. Nos. 5,630,811 and 5,658,323 to Miller disclose a method and apparatus for dermatology treatments for lesions and hair removal using a modified laser device. The specific target for the laser radiation is the melanin within the hair shaft and within the melanocytes lining of the follicular duct. Pulse width is controlled to provide a direct thermal effect from a single pulse.

U.S. Pat. No. 5,647,866 to Zaias discloses a method of hair depilation through the application of pulsed laser energy having a wavelength readily absorbed by hemoglobin. The process of selective photothermoloysis is used by the laser to focus on a particular region in the epidermis to be irradiated. The pulse duration or time period (30 to 40 nanoseconds) is shorter than the thermal relaxation time for melanin in hair.

U.S. Pat. No. 5,683,380 to Eckhouse discloses a method and apparatus for removing hair (depilation) using a single high intensity pulsed flashlamp (not a laser) which emits a broad spectrum of pulsed incoherent light that is polychromatic. Because of the broad spectrum of wavelengths emitted by the flashlamp, only part of the light energy is absorbed by the hair, making it inefficient for permanent hair removal, although it does provide temporary hair loss.

None of these prior art patents disclose the particular structure of the present invention of a laser apparatus and method using two or more lasers coupled with a sequencer for safe and permanent hair removal.

Accordingly, it is an object of the present invention to provide an improved laser apparatus and method which supplies a high level of laser energy to heat a hair follicle and hair follicle shaft to cause permanent damage to that hair follicle and shaft, and yet spare the skin from burning, thus providing a safe and permanent method of hair removal.

Another object of the present invention is to provide an improved laser apparatus employing two or more lasers being coupled by a sequence control device, and two or more fiber optic cables which are joined to form a common fiber optic cable which carries pulses of laser light which have been sequentially emitted from two or more lasers for the purpose of permanently and safely removing a plurality of hair follicles from the skin area of a patient.

Another object of the present invention is to provide an improved laser apparatus having a handpiece for ease of use by the operator in directing the laser pulses at the skin to rapidly remove large areas of hair on almost any body area, such as on the face, hands, arms, legs, breasts, stomach and the like, where such treatment provides a low discomfort level to the patient.

Another object of the present invention is to provide an improved laser apparatus and method for treatment of other cutaneous conditions (in addition to hair), such as the treatment of leg veins, spider veins, angiomas, lesions, other vascular anomalies and other dermatological conditions affecting the skin of a patient.

Another object of the present invention is to provide two or more pulsed lasers coupled by a sequence control device for emitting laser energy through a common optical delivery system which delivers simultaneous or sequential pulsed laser energy from the two or more pulsed lasers.

Another object of the present invention is to provide an improved laser apparatus and method for adjusting pulse width and the time delay between pulses to customize treatment and the energy delivered to the spot being treated according to skin color, hair color, hair diameter and the anatomic site being treated.

Another object of the present invention is to provide safe and permanent hair removal in a wider range of patients having hairs of all colors and skin of all colors, including patients with dark skin. Generally, the present invention will accommodate all persons having hair which is darker than their skin.

Another object of the present invention is to provide a delay between laser pulses which is shorter than the thermal relaxation time of the hair being treated, so the hair does not cool off between pulses, and wherein the delay between laser pulses is longer than the thermal relaxation time of the skin, so the skin may dissipate heat and cool off between pulses and does not burn.

Another object of the present invention is to provide a method and apparatus wherein the pulse width and delay between pulses may be varied to accommodate the thermal relaxation time of each patient's hair and skin.

Another object of the present invention is to provide an improved laser apparatus and method that is easy to use, and the laser apparatus is durable, light-weight and easily maintained.

Another object of the present invention is to provide an improved laser apparatus that provides a wider beam area (spot size on the skin) by utilizing two or more pulsed lasers coupled by a sequencer for delivering more laser energy to each spot allowing the spot size to be made larger for faster treatment.

A further object of the present invention is to provide an improved laser apparatus that is simple to manufacture and assemble in an economical manner, and is cost effective for the user.

SUMMARY OF THE INVENTION

In accordance with the present invention, there is provided a laser apparatus and method for permanently, safely, and quickly removing a plurality of hair follicles or blood vessels from the skin of a patient, including patients with dark skin. The laser apparatus includes a housing having at least first and second lasers contained therein for emitting at least first and second pulses of coherent light energy; first and second fiber optic multi-strand bundles connected to the first and second lasers, respectively, for transmitting the first and second pulses of coherent light energy from the first and second lasers; the first and second fiber optic bundles connected to form a common fiber optic bundle for combining and transmitting at least the first and second pulses of coherent light energy from each of the first and second lasers through the common fiber optic bundle; and a sequence control device for controlling the first and second lasers to emit at least the first and second pulses of coherent light energy either sequentially or simultaneously, with a time delay between pulses less than the thermal relaxation time of the hair being treated, which typically is less than 100 milliseconds. The laser apparatus further includes a handpiece for holding a section of the common fiber optic bundle for directing at least the first and second pulses of sequential or simultaneous pulses of coherent light energy from each of the first and second lasers to a selected spot of the patient's skin to remove a plurality of hair follicles or blood vessels. In alternate embodiments, other optical delivery systems may be employed. These may include an articulated laser arm assembly, or a switching device which switches a collecting lens between the two lasers.

A method of removing hair or blood vessels from the skin of a patient is provided using a laser apparatus and method having at least first and second lasers, a sequence control device and an optical delivery system which includes the steps of controlling the first and second lasers to emit at least first and second pulses of coherent light energy either sequentially or simultaneously, transmitting at least the first and second pulses of coherent light energy to the same spot on the skin of the patient through a common light transmission pathway, irradiating the same spot on the skin containing the hair or blood vessels with the first and second sequential or simultaneous pulses of coherent light energy transmitted through the common light transmission pathway from the first and second lasers, pulsing one of the first and second lasers at a specific wavelength in the range of 550 to 1200 nanometers, at a specific power level in the range of 5 to 80 Joules/cm$^2$, for a specific pulse duration in the range of ½ to 40 milliseconds, having a specific pulse delay between pulses in the range of 5 to 100 milliseconds, and a specific beam diameter in the range of 4 to 50 millimeters on the treatment area; and pulsing the other one of the first and second lasers at a specific wavelength in the range of 550 to 1200 nanometers, at a specific power level in the range of 5 to 80 Joules/cm$^2$, for a specific pulse duration in the range of ½ to 40 milliseconds, having a specific pulse delay between pulses in the range of 5 to 100 milliseconds, and a specific beam diameter in the range of 4 to 50 millimeters on the treatment area.

The new technology requires that high energy laser pulses be delivered in rapid succession to exactly the same area of the skin. The maximal energy is delivered to the hair germinative apparatus using two or more long pulses, with the pulses repeated at a time interval shorter than the thermal relaxation time of the hair being treated. For most patients, this means two or more high-energy (10–40 Joules/cm$^2$) long duration (2 to 30 milliseconds) pulses, separated by 10 to 30 milliseconds, each with a large (e.g., 10 millimeters or greater) spot size. None of the currently-produced lasers are able to produce these results. The 10 to 30 milliseconds delay between pulses must be selected to be shorter than the thermal relaxation time of the hair being treated, so the hair does not cool off between the pulses.

For example, short pulse duration lasers (with a pulse duration measured in nanoseconds) can repeat rapidly, but these are not suitable for optimal hair removal. All of the new hair removal lasers (ruby, alexandrite, diode) are long pulse lasers. Most of these recycle every 1000 milliseconds, with the fastest recycling every 200 milliseconds. The repetition rate that is necessary, however, is over ten times faster. The new laser apparatus of the present invention is able to accomplish these goals.

BRIEF DESCRIPTION OF THE DRAWINGS

Further objects, features, and advantages of the present invention will become apparent upon consideration of the detailed description of the presently-preferred embodiments, when taken in conjunction with the accompanying drawings wherein:

FIG. 5A is a graph showing the time profile and the optical intensity field performance for the twin laser apparatus of the present invention versus the prior art laser;

FIG. 5J is a graph showing the distance profile and the optical intensity field performance for the lasers used during the hair removal process.

DETAILED DESCRIPTION OF THE PREFERRED EMBODIMENT

Figure 1:
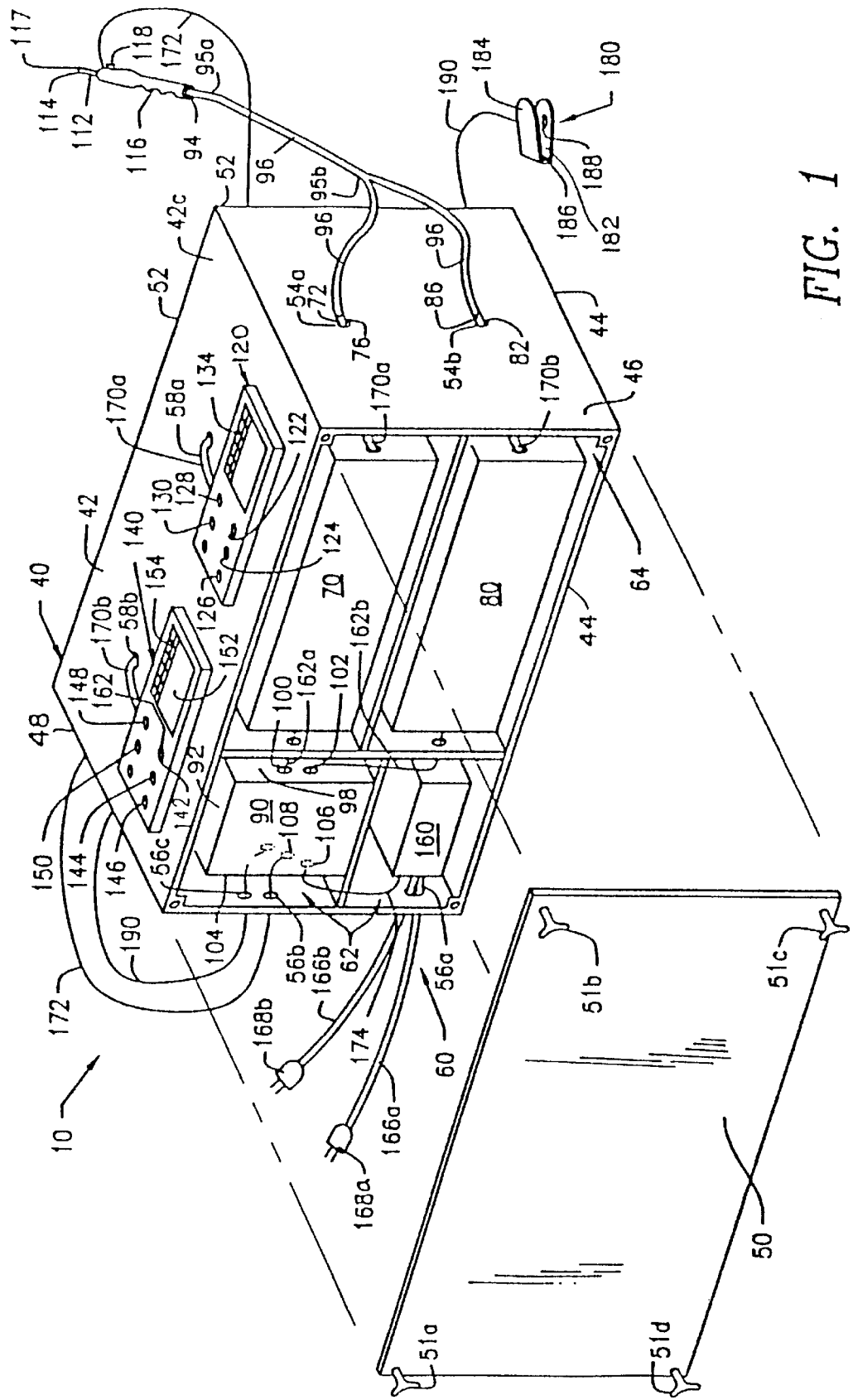
FIG. 1 is a perspective view of the laser apparatus of the preferred embodiment of the present invention showing the housing, having a pair of control panels thereon, the two lasers, the flexible conduit having a common fiber optic bundle therein, the laser handpiece having thereon an operating pulse firing button, and the foot pedal switch assembly having an activation firing button thereon, shown in an operational mode.
Figure 1A:
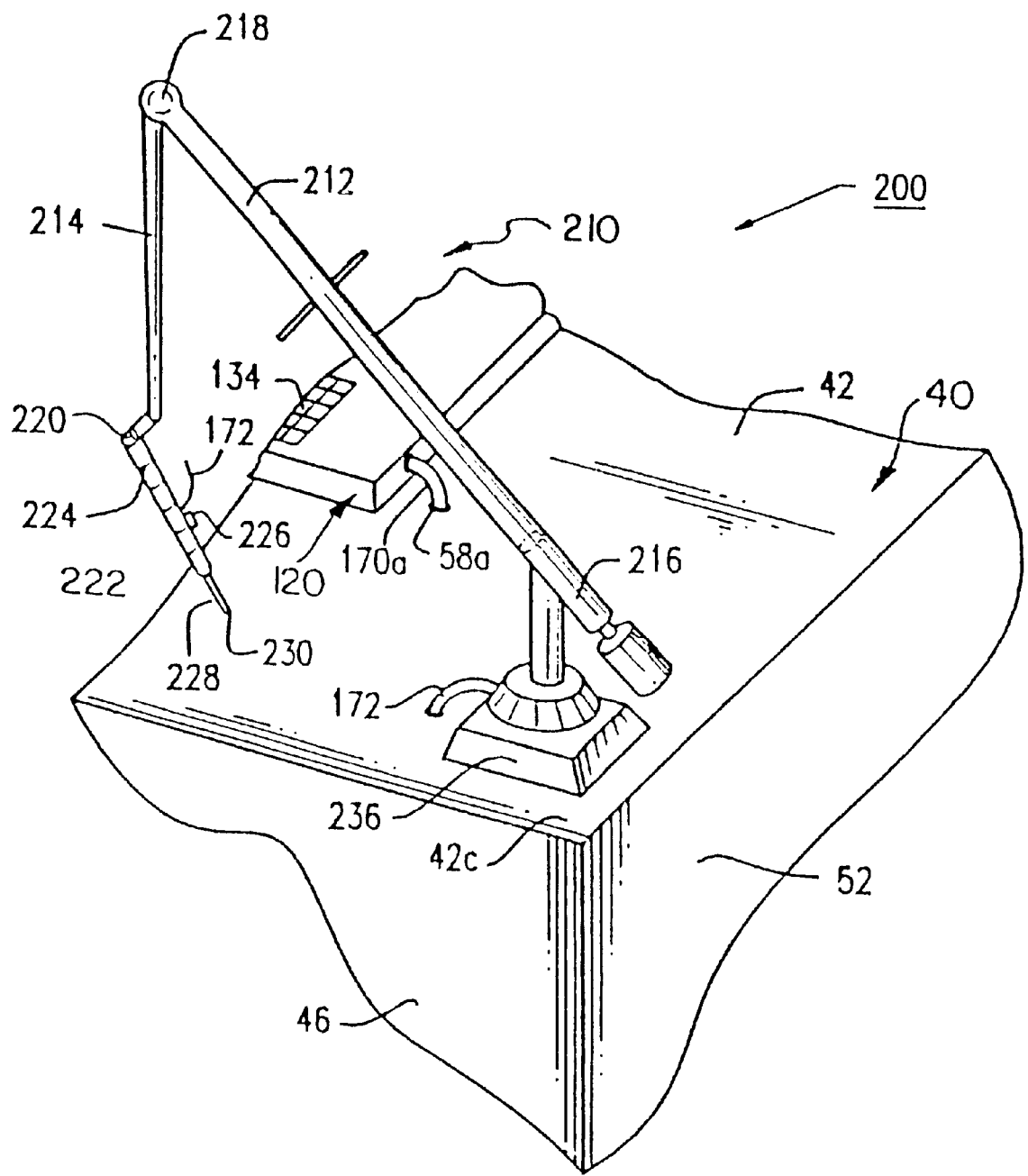
FIG. 1A is a perspective view of the laser apparatus of the present invention showing the alternate embodiment of the articulated laser arm assembly and its component parts thereon.
Figure 2:
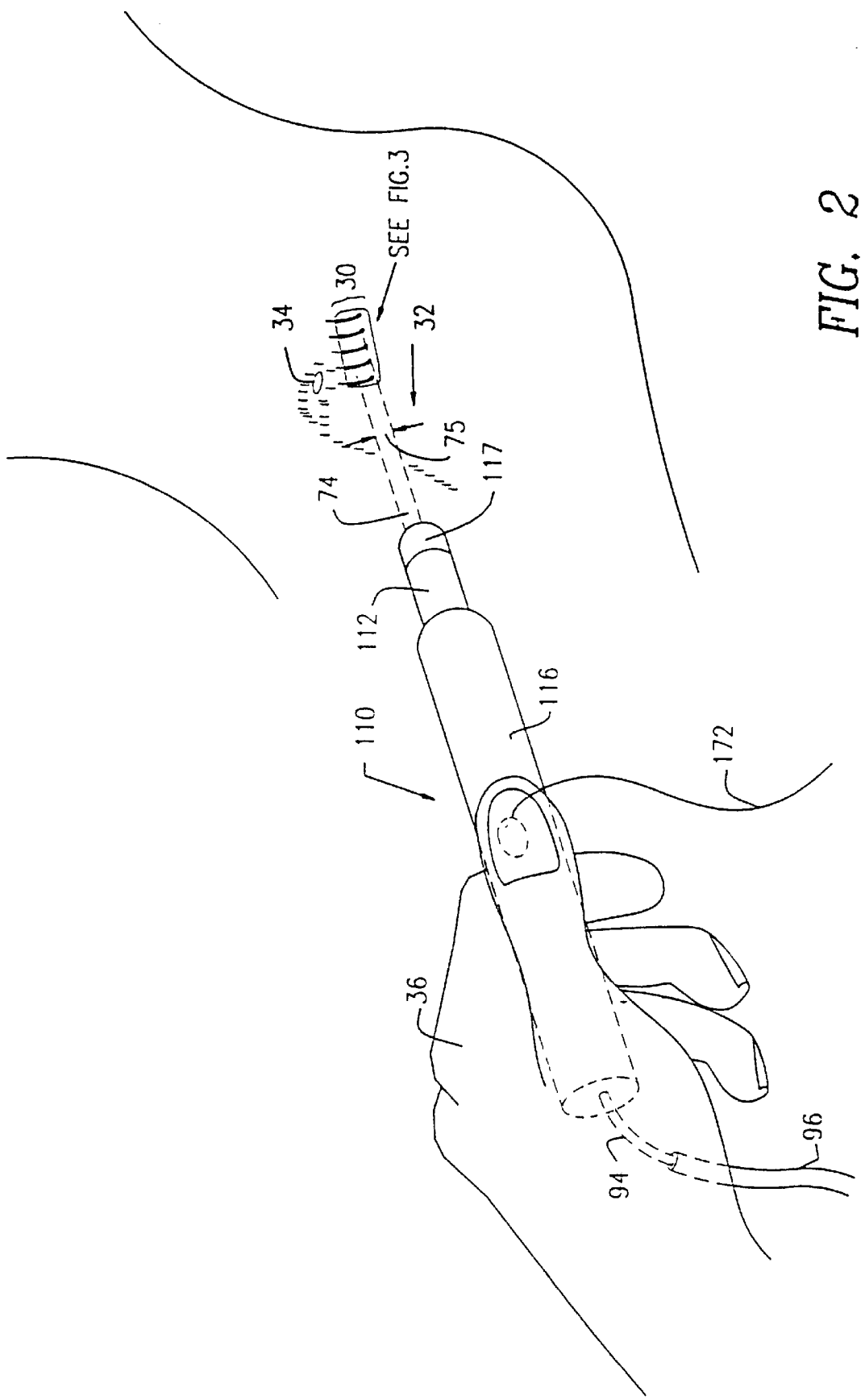
FIG. 2 is an enlarged perspective view of the laser apparatus of the present invention showing the flexible conduit and the laser handpiece having a pulse fire button thereon, shown in an operational mode.

The improved laser apparatus 10 and method thereof for permanently removing a plurality of hair follicles 20 from a patient's skin area 14, or for removing blood vessels 28 such as veins and capillaries, are represented in detail by FIGS. 1, 1A, 2 through 5A to 5J and 6. The laser apparatus 10 of the present invention, as shown in FIGS. 1 and 2 of the drawings, includes a laser housing 40 having therein a first laser device 70, a second laser device 80, a sequence control device 90 and an electrical panel box 160. Additionally, laser apparatus 10 also includes an optical delivery system having first and second multi-strand fiber optic bundles 76 and 86 connected to the laser devices 70 and 80, respectively. Fiber optic bundles 76 and 86 are combined to form a common fiber optic multi-strand bundle 94 and a laser handpiece 110 having a pulse firing button 118 thereon. Handpiece 110 is attached at one end 95a to the common fiber optic bundle 94.

Laser housing 40, as shown in FIG. 1, includes a top wall 42, a bottom wall 44, a front wall 46, a rear wall 48, and side walls 50 and 52, all being integrally connected to form a substantially rectangular shaped configuration which forms an interior chamber 60. The interior chamber 60 includes a first compartment 62 for holding and containing therein the first laser device 70, a second compartment 64 for holding and containing therein the second laser device 80, and a third compartment 66 for holding and containing therein the sequence control device 90 and the electrical panel box 160.

Figure 6:
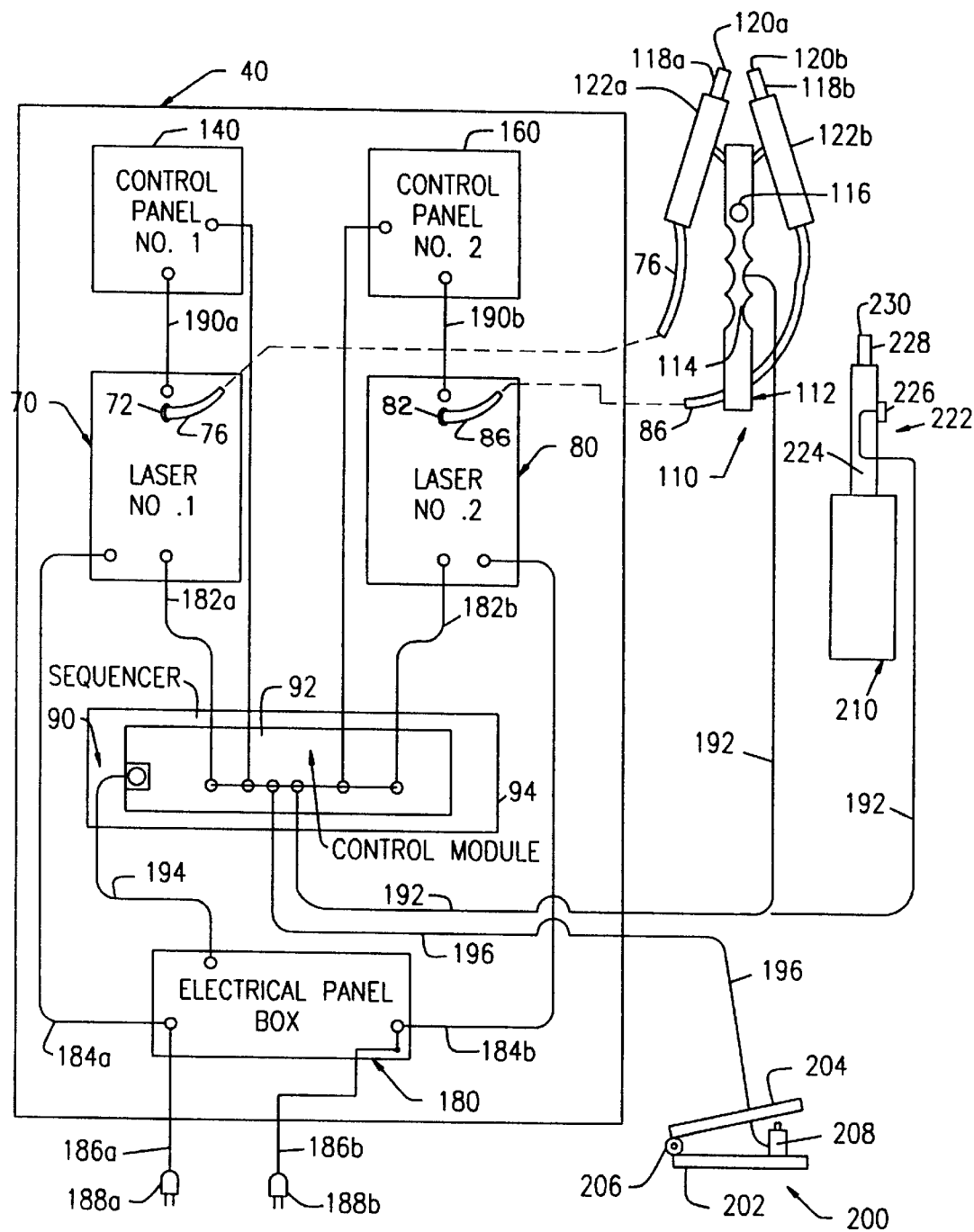
FIG. 6 is an electrical schematic block diagram of the laser apparatus of the present invention showing the electrical connections of the major component parts therein.

First laser device 70, as shown in FIG. 1, includes a laser projector lens 72 of a specific wavelength for producing a first coherent laser beam 74 having a laser beam diameter 75 of a given width. The laser projector lens 72 is attached to the first multi-strand fiber optic bundle 76 for transmitting pulses of light energy (laser beam 74) from the first laser device 70 through the first fiber optic bundle 76. First laser device 70 is electrically connected to the laser sequence control device 90, to the first laser programmable control panel 120, and to the electrical panel box 160 via electrical lines 162a, 170a, and 164a, respectively, as shown in FIG. 6.

Second laser device 80, as shown in FIG. 1, includes a laser projector lens 82 of a specific wavelength for producing a second coherent laser beam 84 having a laser beam diameter 85 of a given width. The laser projector lens 82 is attached to the second multi-strand fiber optic bundle 86 for transmitting the pulses of light energy (laser beam 84) from the second laser device 80 through the second fiber optic bundle 86. Second laser device 80 is electrically connected to the laser sequence control device 90, to the second laser programmable control panel 140, and to the electrical panel box 160 via electrical lines 162b, 170b, and 164b, respectively, as shown in FIG. 6.

Each laser device 70 and 80 is individually adjusted for energy level (Joules/cm$^2$), pulse width duration (ms), spot size (mm) and wavelength (nm) via each of the laser programmable control panels 120 and 140, respectively.

Laser devices 70 and 80 may be selected from the group consisting of an alexandrite laser, a ruby laser, a diode laser, an ND:YAG laser, an infrared laser, and the like. An alexandrite laser has a specific wavelength of 755 nm; a ruby laser has a specific wavelength of 694 nm, a diode laser can be set at any wavelength in the range of 550 to 900 nm; and an ND:YAG laser has a specific wavelength of 1064 nm. The most effective wavelengths for permanent hair removal are in the range of 550 nm to 900 nm when using the alexandrite, ruby and/or diode lasers.

Figure 3:
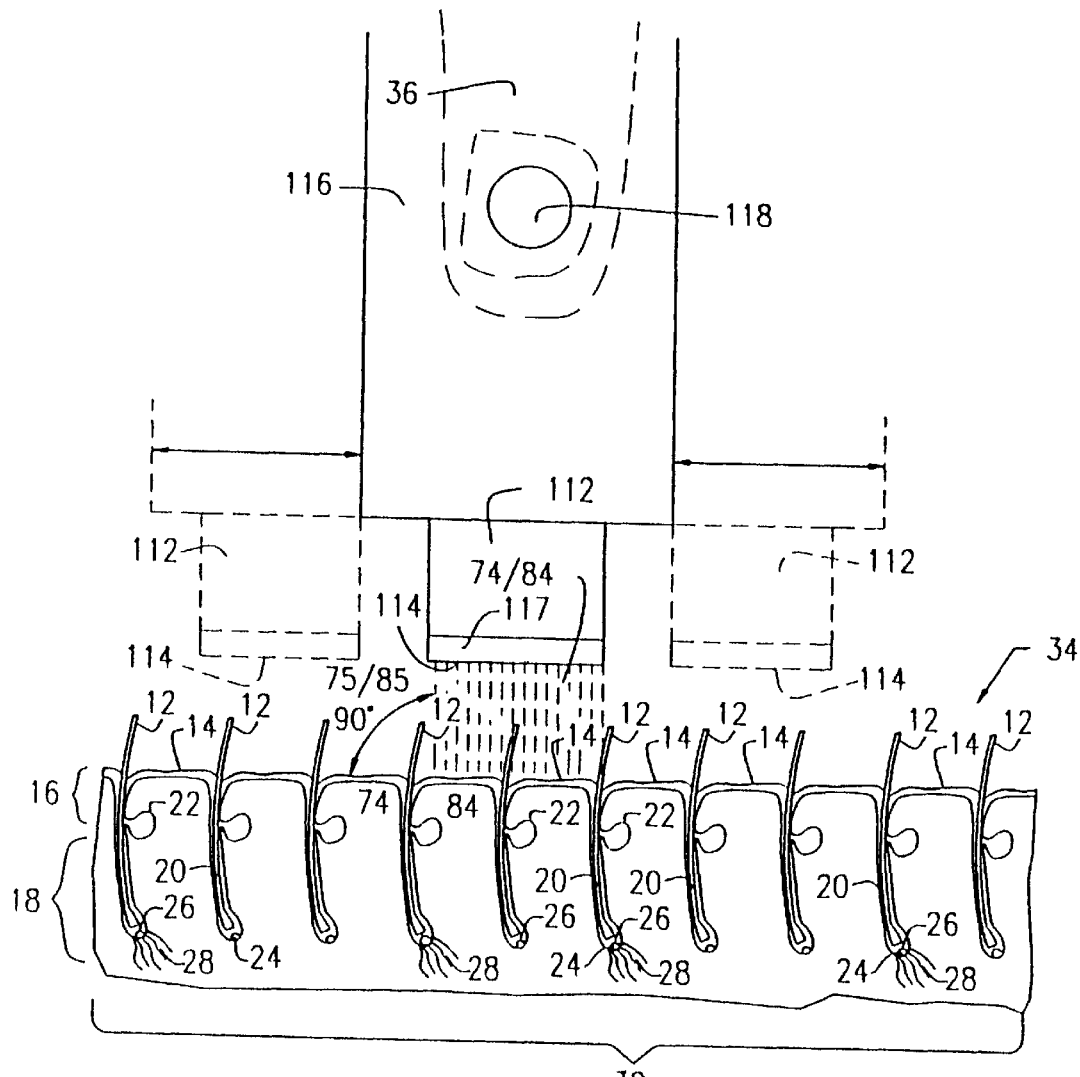
FIG. 3 is a cross-sectional view of a plurality of hair shafts within a region of skin tissue being irradiated with a laser beam from the laser handpiece of the present invention.

The laser sequence control device 90 is used for controlling the sequential or simultaneous pulsing of the two laser beams 74 and 84 from laser devices 70 and 80, respectively, and includes a sequencer laser control module 90M for controlling the lasers 70 and 80 to sequentially or simultaneously emit pulses of coherent light energy when the laser operator depresses the pulse firing button 118 on laser handpiece 110. The sequencer laser control module 90M may be in the form of a microprocessor or an electronic timing device. Laser beams 74 and 84 destroy and permanently remove the plurality of hair follicles 20 from the skin area 14 of a patient, as shown in FIGS. 1 to 3 of the drawings. The laser sequence control device 90 includes a substantially rectangular shaped housing 92 for holding the sequencer laser control module 90M therein. Housing 92 includes a front wall 98 with openings 100 and 102 for receiving electrical lines 162a and 162b from laser devices 70 and 80, respectively, being connected to the sequencer laser control module 90M; and includes a rear wall 104 having an opening 106 for receiving an electrical line 174, such that electrical line 174 connects the electrical panel box 160 to the sequencer laser control module 90M, and having an opening 108 for receiving of electrical line 172, such that electrical line 172 connects the pulse fire button 118 to the sequencer laser control module 90M.

As shown in FIG. 1, the front wall 46 of housing 40 includes first and second openings 54a and 54b for receiving the first and second fiber optic bundles 76 and 86 from laser devices 70 and 80, respectively. The rear wall 48 includes a first opening 56a for receiving power lines 166a and 166b connected to the electrical panel box 160, a second opening 56b for receiving electrical line 172 from the pulse fire button 118 to the sequencer control module 90M of laser sequence control device 90, and a third opening 56c for receiving electrical line 190 from the activation laser button 188 of the foot pedal switch assembly 180 to the sequencer control module 90M of sequence control device 90. Top wall 42 includes control panels 120 and 140, as well as openings 58a and 58b for receiving electrical lines 170a and 170b from laser devices 70 and 80, respectively. Left side wall 50 is removably connected to laser housing 40 via connecting means 51a to 51d and is used as an access panel 50 for ease of access by the laser operator for repairing and maintaining the laser devices 70 and 80, the sequence control device 90 and the electrical panel box 160 thereof.

The optical delivery system includes a laser handpiece 110 for receiving common fiber optic bundle 94. Handpiece 110 is used for delivering and emitting the sequentially or simultaneously pulsed laser beams 74 and 84 from common fiber optic bundle 94, under the control of sequencer control module 90M of sequence control device 90. Laser handpiece 110 includes a laser dispersal member 112 having a laser portal opening 114 for receiving common fiber optic bundle 94 and a lens 117 for emitting the first and second laser beams 74 and 84 of laser devices 70 and 80, respectively. Laser handpiece 110 further includes a hand gripping/holding section 116 having a pulse firing button 118 thereon. Pulse firing button 118 is electrically connected to the sequencer control module 90M of sequence control device 90 via electrical line 172. Common fiber optic bundle 94 is sheathed within a flexible conduit 96 for protecting the common fiber optic bundle 94. Handpiece 110 also includes a lens for focusing the laser energy on the spot being treated.

An alternate optical delivery system is available in the form of an articulated laser arm assembly 210 and may be used in place of the fiber optic bundles 76, 86 and 94 and is connected to laser devices 70 and 80, respectively, and laser handpiece 110. The articulated laser arm assembly 210 is also used for transmitting the sequentially or simultaneously pulsed laser beams 74 and 84 from laser devices 70 and 80, respectively. Sequence control device 90 operates in the same manner as in the preferred embodiment. The articulated laser arm assembly 210 is located on the corner section 42c of top wall 42 and is adjacent to the first laser control panel 120 of laser housing 40, as depicted in FIG. 1A of the drawings. Articulated laser arm assembly 210, as shown in FIG. 1A, includes a first arm member 212 pivotally attached to a second arm member 214. As is know in the art, articulated laser arm assembly 210 further includes a first mirror 216, a second mirror 218 and a third mirror 220 for reflecting the sequential or simultaneous coherent light beams (laser beams 74 and 84) through the first and second arm members 212 and 214, respectively. Additionally, articulated laser arm assembly 210, also includes a laser handle member 222 pivotally attached to the second arm member 214. Laser handle member 222 includes a gripping/holding section 224 having a pulse firing button 226 thereon, and a laser dispersal member 228 having a laser portal opening 230 for emitting the first and second laser beams 74 and 84 of laser devices 70 and 80, respectively. The articulated laser arm assembly 210 further includes a base member 236 for attaching to the corner section 42c of top wall 42. Pulse fire button 226 is electrically connected to the sequencer control module 90M of sequence control device 90 via electrical line 172.

Another optical delivery system which may be used is a lens system connected to a common optical delivery path connected to the handpiece. In this arrangement, the output of laser 70 is directed to an angled lens which directs the light to the common optical delivery path. Similarly, the output of laser 80 is directed to an angled lens which also directs the light to the same optical delivery path and to the handpiece. Other optical delivery systems, such as a light path or pipe for a diode laser, may be used.

As shown in FIG. 6, laser devices 70 and 80 are electrically connected to the sequencer laser control module 90M of laser sequence control device 90 via electrical lines 162a and 162b, respectively, as well as to the electrical panel box 160 via electrical lines 164a and 164b, respectively. Electrical power lines 166a and 166b and plugs 168a and 168b are used for wall electrical outlets (not shown) and are electrically connected to the electrical panel box 160 via power lines 166a and 166b for laser devices 70 and 80, respectively. Laser devices 70 and 80 are also electrically connected via electrical lines 170a and 170b to a first laser programmable control panel 120 and to a second laser programmable control panel 140, respectively. The pulse firing button 118 of laser handpiece 110 is electrically connected to the sequencer laser control module 90M via electrical line 172. The activation laser switch/button 188 of foot pedal switch assembly 180 is electrically connected to the sequencer laser control module 90M via electrical line 190. The sequencer laser control module 90M is electrically connected to the electrical panel box 160 via electrical line 174.

The first laser programmable control panel 120 is used for controlling the various output functions of energy/power level, in Joules/centimeters$^2$ (J/cm$^2$), the irradiation pulse width duration in milliseconds (ms), the pulse delay in milliseconds (ms) and the laser beam diameter in millimeters (mm) for the first laser device 70. Control panel 120 includes a plurality of control members 122 to 130 and a visual display screen 132 having a keyboard 134 for programming the aforementioned output functions of energy/power level, pulse width duration, pulse delay, and laser beam diameter 75. The control members include an ON/OFF button 122 for activating and de-activating the first laser device 70; a control knob/selector 124 for adjusting the energy/power level of the first laser device 70; a control knob/selector 126 for adjusting the irradiation pulse width duration (ms) of laser beam 74 of the first laser device 70; a control knob/selector 128 for adjusting the pulse delay of the de-activation time (ms) of laser beam 74 of the first laser device 70; and a control knob/selector 130 for adjusting the laser beam diameter 75 of the first laser device 70. Control panel 120 is electrically connected to laser device 70 via electrical line 170a, as shown in FIG. 6.

The second laser programmable control panel 140 is used for controlling the various output functions of energy/power level in Joules/centimeters$^2$ (J/cm$^2$), the irradiation pulse width duration in milliseconds (ms), the pulse delay in milliseconds (ms) and the laser beam diameter in millimeters (mm) for the second laser device 80. Control panel 140 includes a plurality of control members 142 to 150 and a visual display screen 152 having a keyboard 154 for programming the aforementioned output functions of energy/power level, pulse width duration, pulse delay and laser beam diameter 85. The control members include an ON/OFF button 142 activating and de-activating the second laser device 80; a control knob/selector 144 for adjusting the energy/power level of the second laser device 80; a control knob/selector 146 for adjusting the irradiation pulse width duration (ms) of the laser beam 84 of the second laser device 80; a control knob/selector 148 for adjusting the pulse delay of the de-activation time (ms) of laser beam 84 of the second laser device 80; and a control knob/selector 150 for adjusting the laser beam diameter 85 of the second laser device 80. Control panel 140 is electrically connected to laser device 80 via electrical line 170b, as shown in FIG. 6.

As an alternate to the pulse firing button 118, a foot pedal switch assembly 180 may be used for initiating the firing sequence of laser beams 74 and 84 from laser devices 70 and 80, respectively. Foot pedal switch assembly 180, as shown in FIG. 1 of the drawings, includes a foot pedal base 182 and a foot pedal 184 being connected to the base 182 by a hinge 186. Foot pedal base 182 includes an activation laser switch/button 188 being electrically connected to the sequencer control module 90M via electrical line 190.

METHOD OF THE PRESENT INVENTION

As depicted in FIG. 3, the plurality of hair shafts 12 project below the epidermis region 16 of skin area 14 and into the dermis region 18. Each hair shaft 12 extends down the follicle 20 and includes a sebaceous gland 22 and which at the anagen stage of the hair cycle further includes a follicular papilla 24 within the hair bulb 26 of hair shaft 12. The follicular papilla 24 is supplied with a plurality of small blood vessels 28 that provide the plurality of growing hair shafts 12 with nourishment. The follicular papilla 24 is an essential structure within the follicle matrix structure 30.

In order to assure destruction of the follicular papilla 24 and permanent hair removal, a sufficient laser energy level is required, but it must be delivered in a manner that does not burn the skin. In addition, the depth of penetration of the laser beams must be sufficient to cause permanent removal of hair shaft 12 from the epidermis and dermis regions 16 and 18 of the patient's skin area 14.

As shown in FIGS. 1 through 3 of the drawings, the laser operator (not shown) positions the laser dispersal member 112 of the laser handpiece 110 over a selected treatment area, such as the navel area 34 of the stomach 32 of the patient being treated. The laser dispersal member 112 is positioned, as shown in FIG. 3, by the hand 36 of the laser operator such that the pulsed laser beams 74 and 84 are substantially perpendicular over the selected treatment area, such as a plurality of hair follicles 20 to be removed. Handpiece dispersal member 112 is positioned at the optimum location for directing the pulsed laser beams 74 and 84 to strike the plurality of follicular papilla 24 in order to irradiate them in a proper mode. While the handpiece dispersal member 112 is maintained perpendicular to the skin, it is moved parallel to the plane of the skin along the surface of the skin area 14 for irradiating successive pluralities of hair follicles 20. The handpiece 110 is then moved vertically to the next horizontal line to repeat the removal procedure. The critical regions of the hair follicle matrix structure 30 include hair follicles 20, sebaceous glands 22 and follicular papillas 24 which are irradiated by the pulsed laser beams 74 and 84 being moved across the skin area 14.

Figure 4:
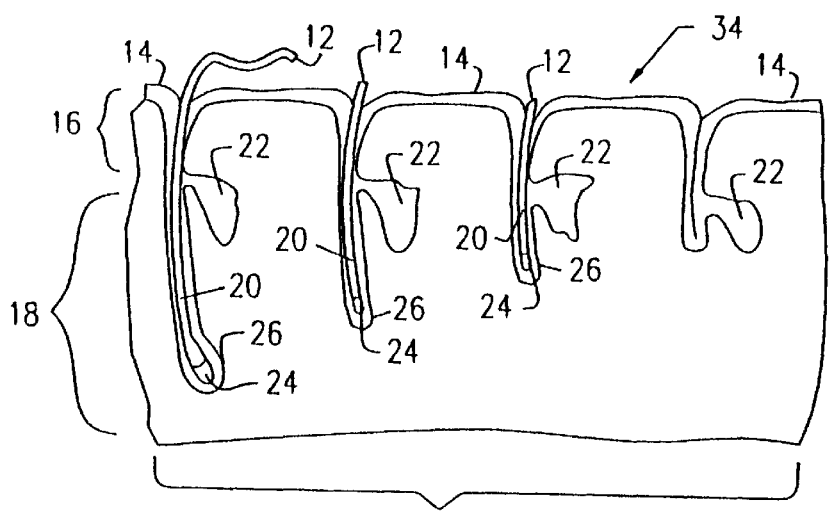
FIG. 4 is a cross-sectional view of a plurality of hair shafts within a region of skin tissue after irradiation by a laser according to the present invention and showing the gradual atrophy of the hair follicle region.

Application of laser pulses 74 and 84 to the plurality of hair follicles 20 and to the plurality of follicular papillas 24 causes selective photothermolysis of the hair germinative apparatus, and more particularly, disruption of the hair follicle matrix structure 30 including vaporization of the deposited melanin, capillary destruction of the papillas 24, as well as vacuolation, edema, gas bubbles and protein denaturation. When the laser pulses 74 and 84 applied to the plurality of hair follicles 20 are of sufficient level, these effects will seriously injure each of the hair follicles 20 and papillas 24 being irradiated thereby permanently damaging the hair germ 26 which is responsible for hair regrowth which results in permanent hair removal. The first laser pulse 74 from laser device 70 heats up the hair follicles 20 and the second laser pulse 84 from laser 80 supplies further heat energy to vaporize the hair follicles 20, as depicted in FIGS. 3 and 4 of the drawings.

A laser apparatus and method using multiple lasers has been provided which, by dividing the laser energy delivery into multiple, individually adjustable pulses, with an adjustable delay between the pulses, allows it to achieve permanent hair removal without burning the skin on both light and dark skinned patients having either fine or coarse hair. The pulse repetition rate (the delay between pulses) is less than the thermal relaxation time (TRT) of the hair being treated, and preferably is longer than the thermal relaxation time (TRT) of the patient's skin. This multiple laser apparatus provides for 1) adjusting, separately, the pulse width and fluence of each laser; 2) a common optical delivery system, so that each pulse is delivered to precisely the same spot; 3) the operator to precisely define the delay between pulses, and adjust this delay according to clinical variables, such as skin color, hair color, and hair coarseness; and 4) the delivery of these pulses much more rapidly than previous long pulse lasers, so that the delay between pulses is less than the TRT of the patient's skin. Treatment may therefore be customized according to skin color, hair color, hair diameter, and the anatomic site being treated, as depicted by Examples G and H of FIGS. 5H and 5I, respectively.

The new technology requires that high energy laser pulses be delivered in rapid succession to exactly the same area of the skin. The maximal energy is delivered to the hair germinative apparatus using two or more long pulses, with the pulses repeated at a time interval shorter than the thermal relaxation time of the hair being treated. For most patients, as depicted by Examples A to D of FIGS. 5B to 5E of the drawings, respectively, this means two or more high-energy (10–40 Joules/cm$^2$) long duration (2 to 30 milliseconds) pulses, separated by 10 to 30 milliseconds, each with a large (e.g., 10 millimeters or greater) spot size. None of the currently-produced lasers are able to produce these results. The 10 to 30 milliseconds delay between pulses must be selected to be shorter than the thermal relaxation time of the hair being treated, so the hair does not cool off between the pulses.

For example, short pulse duration lasers (with a pulse duration measured in nanoseconds) can repeat rapidly, but these are not suitable for optimal hair removal. All of the new hair removal lasers (ruby, alexandrite, diode) are long pulse lasers. Most of these recycle every 1000 milliseconds, with the fastest recycling every 200 milliseconds, as shown in FIG. 5A of the drawings. The repetition rate that is necessary, however, is over ten times faster. The new laser apparatus of the present invention is able to accomplish these goals.

The clinical circumstances which the laser operator encounters include situations where the characteristics of the laser energy must be dramatically changed in order to deliver maximal energy without skin damage. The reason for this is that many variables affect the way laser energy is absorbed. For instance, dark hair absorbs more laser energy than light hair, as does dark skin. Coarse hair retains the heat caused by absorption of laser energy longer than fine hair, and skin cools faster than hair. By taking advantage of these differential rates of heating and cooling one can fashion a series of laser energy pulses that will selectively remove hair.

For example, an African-American patient with brown skin and coarse, black hair would need to have the energy delivered slowly with a relatively long delay between pulses. However, the optimal time delay selected is not long enough to allow the hair to cool, but is long enough to allow the skin to cool. In this manner, the delay between pulses is selected to be less than the TRT of the hair, but more than the TRT of the skin. The second pulse is then emitted, heating the hair more, this time causing permanent destruction of the hair. The skin again heats up, but not enough to cause damage. As shown by Example E of FIG. 5F, the first laser pulse 74 is long, e.g. 20 ms, with low energy (e.g. 10 Joules/cm$^2$). The time delay would be relatively long (e.g. 40 ms), and then the second laser pulse 84 (from the second laser device 80) is emitted with a long pulse width (e.g. 15 ms) and low energy (e.g. 8 Joules/cm$^2$). Thus, 18 Joules/cm$^2$ is delivered safely in two pulses, whereas a single pulse of 18 Joules/cm$^2$ might burn this patient's dark skin.

A Caucasian patient with light brown, fine hair, and light, untanned skin requires much greater energy delivered in order to achieve permanent hair removal. Light, fine hair absorbs little laser energy, but even light skin will absorb some laser energy, which is why pulsed energy delivery, with a delay to allow skin cooling, allows the delivery of more laser energy, safely, to the hair germinative apparatus. In this situation, as shown by Example F of FIG. 5G, one would use a relatively short first laser pulse 74 (e.g. 5 ms) with a high energy level (e.g. 35 Joules/cm$^2$) from laser device 70; a short time delay between pulses (e.g. 10 ms) since light skin cools faster; and a short second laser pulse 84 (e.g. 5 ms) with a somewhat less energy level (e.g. 20 Joules/cm$^2$) from the second laser device 80. Thus, 55 Joules/cm$^2$ are thereby delivered safely in two pulses to a patient in whom 40 Joules/cm$^2$ delivered in a single pulse might burn the skin.

Figure 5B:
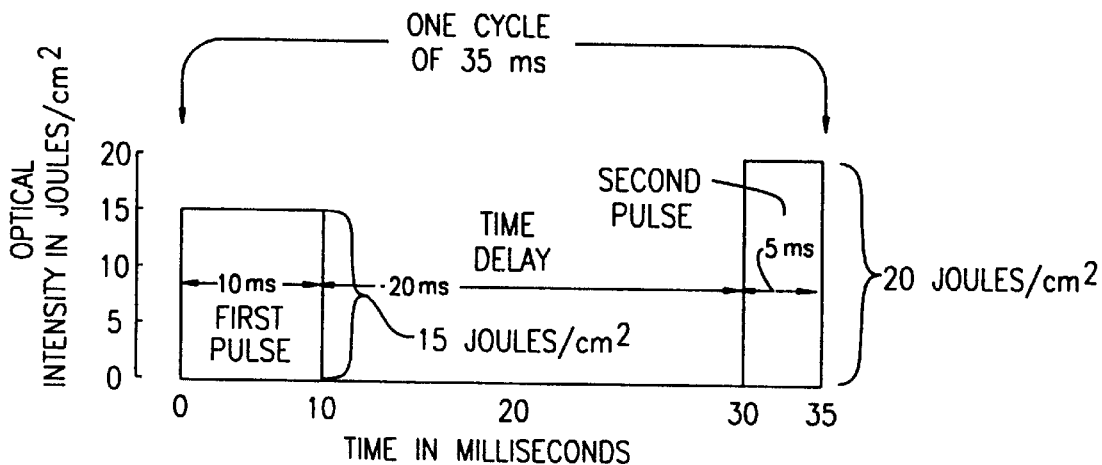
FIG. 5B is a graph showing the time profile and the optical intensity field performance for the lasers used during the sequential pulsing of the coherent light energy for the hair removal process.
Figure 5C:
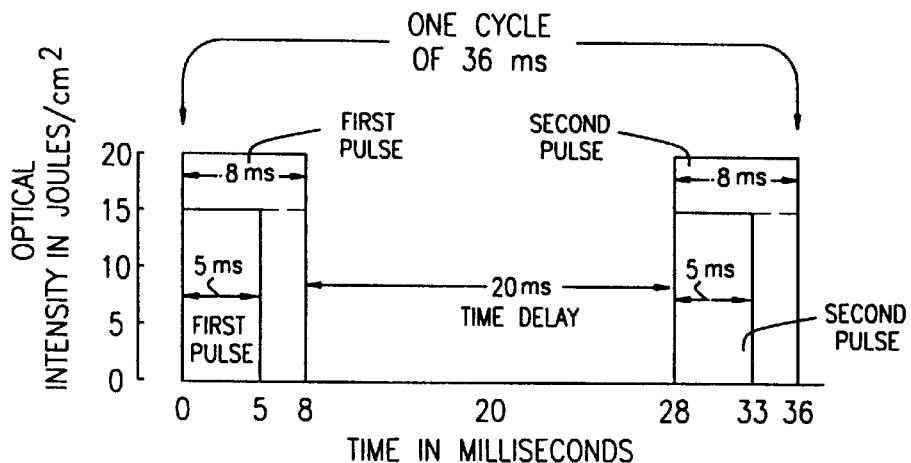
FIG. 5C is a graph showing the time profile and the optical intensity field performance for the lasers used during the simultaneous pulsing of the coherent light energy for the hair removal process.
Figure 5D:
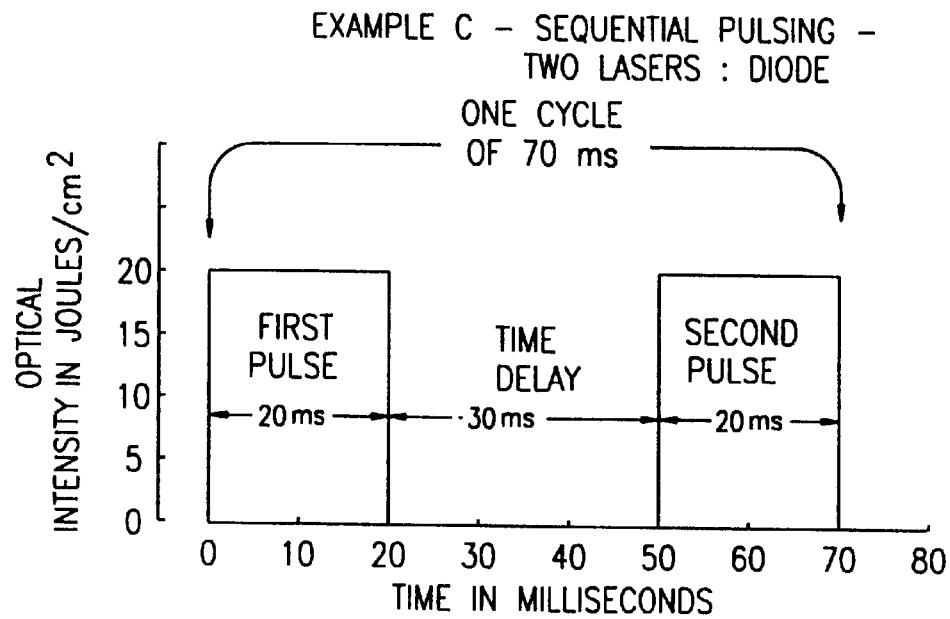
FIG. 5D is a graph showing the time profile and the optical intensity field performance for the sequential pulsing of coherent light energy of two diode lasers for the hair removal process.
Figure 5E:
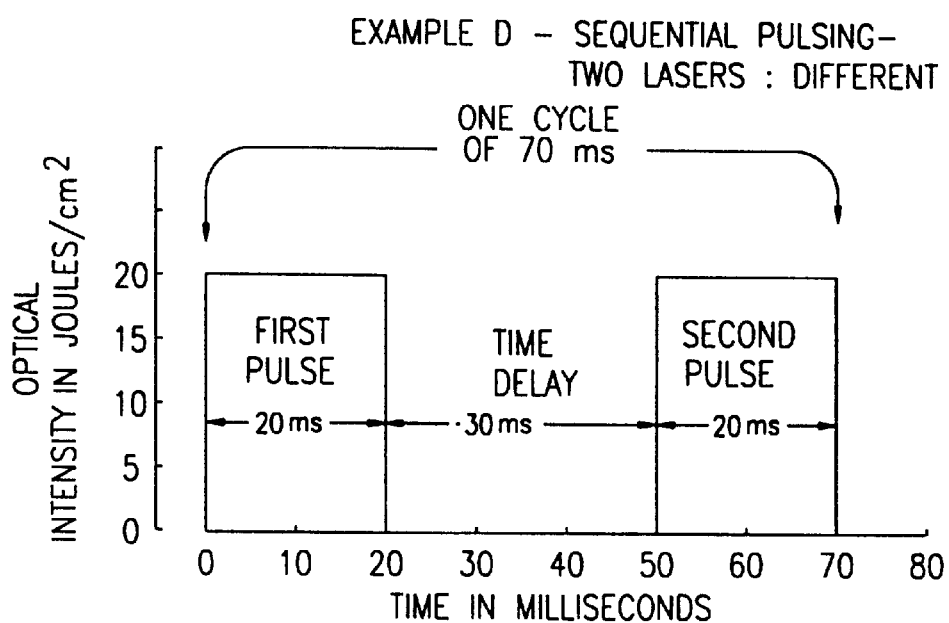
FIG. 5E is a graph showing the time profile and the optical intensity field performance for the sequential pulsing of coherent light energy of two different lasers (e.g. an alexandrite laser and a ruby laser) for the hair removal process.
Figure 5F:
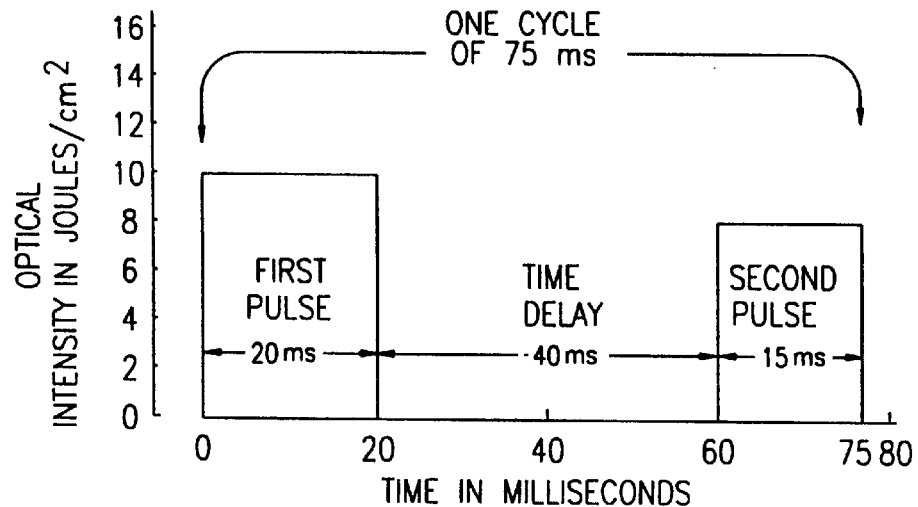
FIG. 5F is a graph showing the time profile and the optical intensity field performance for the sequential pulsing of coherent light energy of two lasers for the hair removal process and treatment of African-American patients.
Figure 5G:
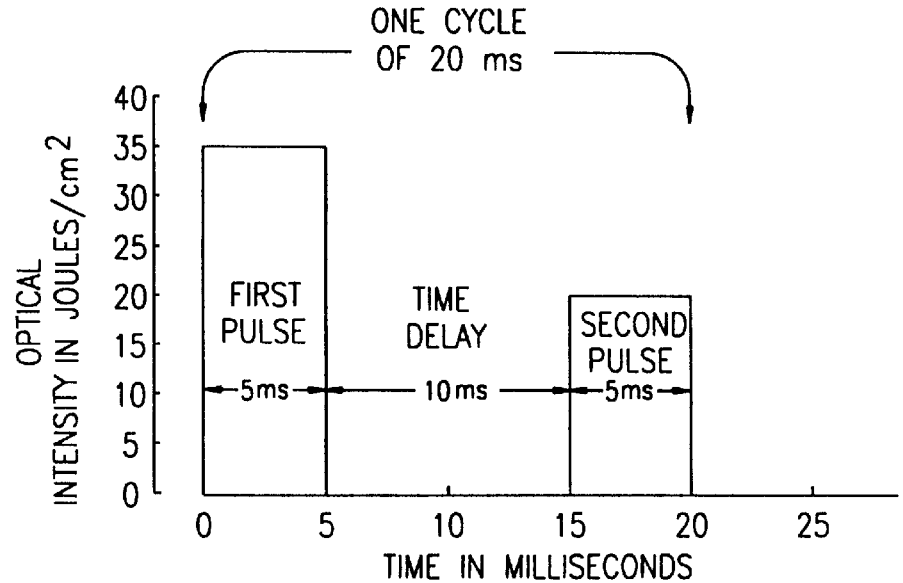
FIG. 5G is a graph showing the time profile and the optical intensity field performance for the sequential pulsing of coherent light energy using two lasers for the hair removal process and treatment of Caucasian patients with fair skin.
Figure 5H:
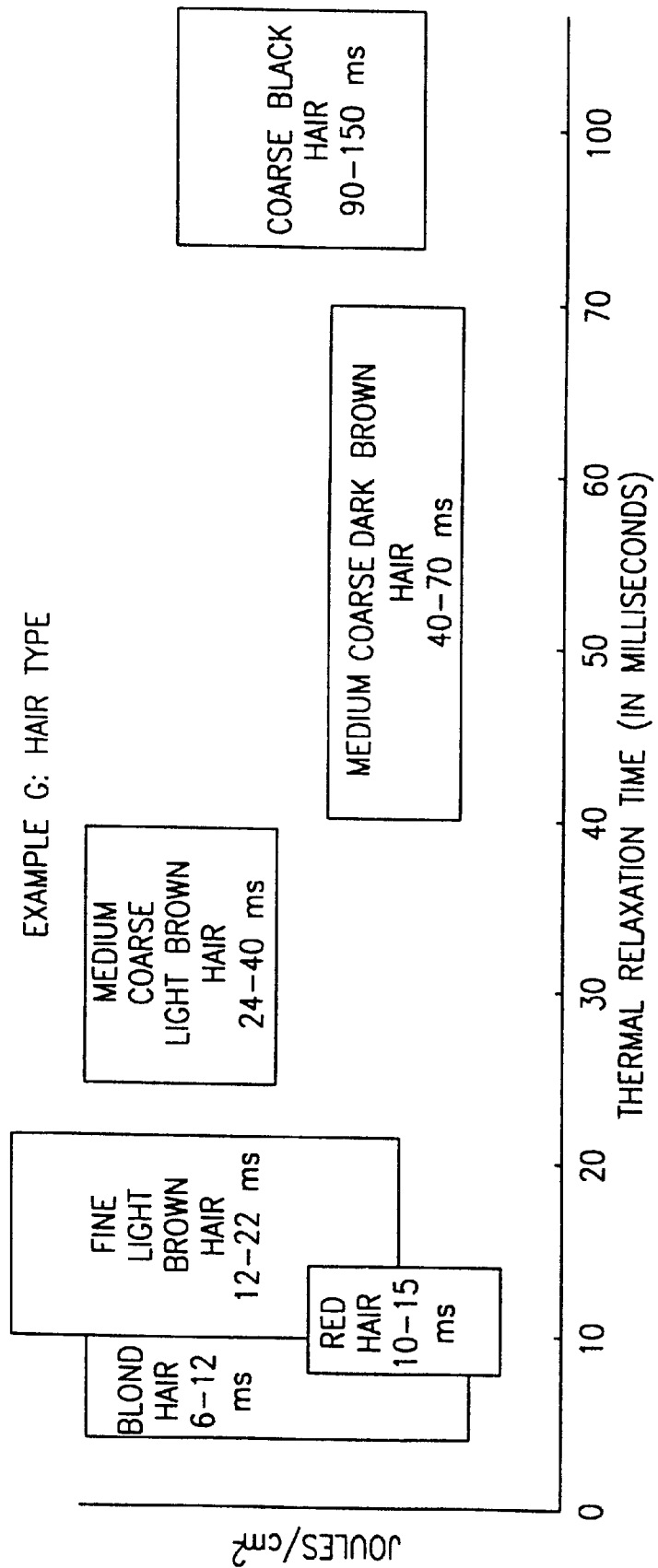
FIG. 5H is a graph showing the thermal relaxation time (TRT) profile and the optical intensity field performance of different hair types for the hair removal process.
Figure 5I:
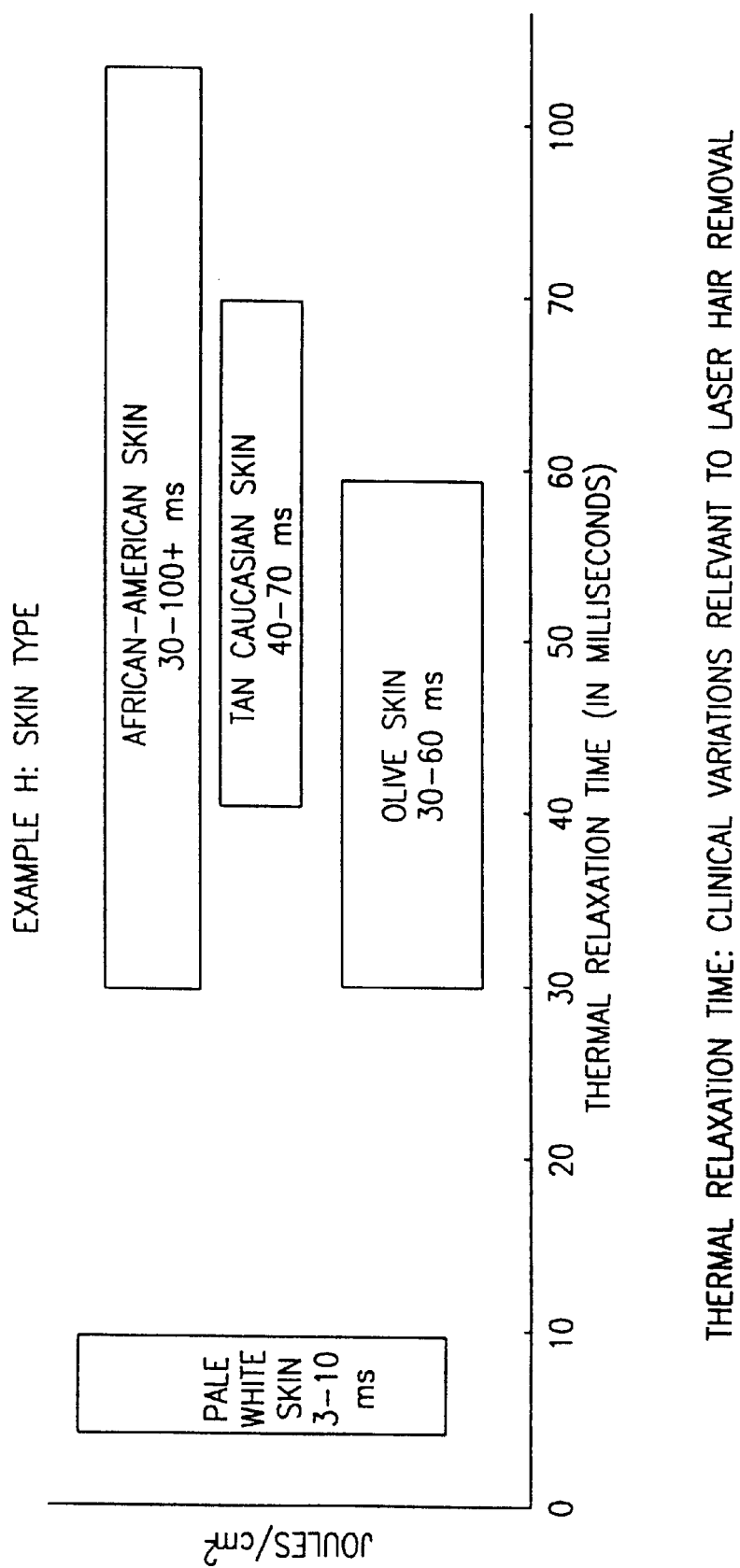
FIG. 5I is a graph showing the thermal relaxation time (TRT) profile and the optical intensity field performance of different skin types for the hair removal process.

The actual irradiating of the plurality of hair follicles 20 is accomplished by the laser operator depressing the pulse firing button 118 of laser handpiece 110 which in turn emits laser pulses 74 and 84 in a sequenced pulsed cycle or a simultaneous pulsed cycle over the designated treatment area 30, as shown in FIGS. 2, 3, 5A, 5B and 5C of the drawings. In the Example A of sequential pulsing of two lasers, as shown in FIG. 5B, laser beam 74 of laser device 70 is pulsed for an irradiation time of preferably 10 milliseconds (irradiation time can be varied in the range of ½ to 40 milliseconds for each of the laser beams 74 and 84) at 15 Joules/cm$^2$. Then a pulse delay duration time of preferably 20 milliseconds is allowed for cooling the skin area 14 in order to prevent burning (pulse delay duration time between laser devices 70 and 80 can be varied in the range of 5 to 100 milliseconds). Laser beam 84 of laser device 80 is then pulsed for an irradiation time of preferably 5 milliseconds (ms) at 20 Joules/cm$^2$ with a delay duration time of preferably 20 milliseconds. A complete cycle of pulsed irradiation and delay time is thus 35 milliseconds delivering a total of 35 Joules/cm$^2$ which is sufficient to permanently remove the plurality of hair follicles 20 of the patient's skin area 14 being treated by laser beams 74 and 84 of laser apparatus 10 of the present invention.

In the above Example A of FIG. 5B, the two laser devices 70 and 80 firing their respective pulses 74 and 84 in sequence with a delay time between them, laser devices 70 and 80 are controlled by sequence control device 90 so that laser device 70 emits the 10 ms pulse at an energy level of 15 Joules/cm$^2$, then there is the 20 ms delay which allows the skin spot being treated to dissipate heat and slightly cool, and then laser device 80 emits a 5 ms pulse at an energy level of 20 Joules/cm$^2$ to the same spot. Thus, the same treatment spot receives 35 Joules/cm$^2$ of energy in 35 ms without burning the skin. Thus, an increased amount of energy is delivered to the same spot safely and without burning the skin. The invention also allows the treated spot size to be increased (e.g. from 10 mm in diameter to 15 mm) and still be effective in permanently and safely removing the hair, as depicted by FIG. 5J of the drawings. Thus the treatment procedure can proceed more rapidly.

The foregoing procedure is made possible with the present invention because there are at least two (2) laser devices 70 and 80 operating with a sequencer control device 90 and this allows the time between pulses to be controlled and substantially reduced to less than 100 ms, e.g. 20 ms. This short delay between pulses is enough time to allow the spot being treated to dissipate heat and cool so that it can receive more energy (e.g. 35 Joules/cm$^2$) safely without burning the skin and permanently remove the hair. In addition, the 35 Joules/cm$^2$ is enough energy to burn the hair follicles over a larger spot size (e.g. 15 mm v. 10 mm) so that a larger area of the patient can be treated in substantially less time. Spot size 75 may be circular or rectangular and a grid pattern may be used for ease of moving handpiece 110 across the patient's skin 14.

Laser devices 70 and 80 may be pulsed in a number of different modes to obtain the desired result, which include sequential pulsing, as described above, or simultaneously pulsing, or a combination of both. As shown by Example B in FIG. 5C of the drawings, the sequence control device 90 may be set to simultaneously emit a 5 ms pulse from laser device 70 and a 8 ms pulse from laser device 80, so that the pulses overlap for 5 ms and then there is only one laser pulse for the next 3 ms.

Alternatively, the articulated laser arm assembly 222 with laser dispersal member 228 and pulse firing button 226, as shown in FIG. 1A, is operated in a similar manner as in the preferred embodiment described above.

As shown in FIG. 4, the laser-damaged follicles 20 will gradually recede due to destruction of the follicle matrix structure 30, including disruption of blood flow from the blood vessel capillaries 28 to each of the papillas 24. The hair follicles 20 show gradual atrophy without a blood supply thereby causing permanent hair removal.

Different types of hair and skin pigmentation, and different cooling times of the epidermis, and hair follicles of different sizes, as well as the location of body hair to be removed will require different sequences of laser treatment to fit the individual needs of the patient undergoing the therapeutic laser treatment for permanent hair removal. As shown by Example D of FIG. 5E, this laser treatment of pulsed laser beams 74 and 84 from different lasers allows the laser operator to individually augment each of the output functions of wavelength, energy/power level, pulse width duration, pulse delay and laser beam diameters 75 and 85 for the particular patient using first and second control panels 120 and 140 that control the first and second laser devices 70 and 80, respectively, of laser apparatus 10 of the present invention.

ADVANTAGES OF THE PRESENT INVENTION

Accordingly, an advantage of the present invention is that it provides an improved laser apparatus and method which supplies a high level of laser energy to heat a hair follicle and hair follicle shaft to cause permanent damage to that hair follicle and shaft, and yet spare the skin from burning, thus providing a safe and permanent method of hair removal.

Another advantage of the present invention is that it provides for an improved laser apparatus employing two or more lasers being coupled by a sequence control device, and two or more fiber optic cables which are joined to form a common fiber optic cable which carries pulses of laser light which have been sequentially emitted from two or more lasers for the purpose of permanently and safely removing a plurality of hair follicles from the skin area of a patient.

Another advantage of the present invention is that it provides for an improved laser apparatus having a handpiece for ease of use by the operator in directing the laser pulses at the skin to rapidly remove large areas of hair on almost any body area, such as on the face, hands, arms, legs, breasts, stomach and the like, where such treatment provides a low discomfort level to the patient.

Another advantage of the present invention is that it provides for an improved laser apparatus and method for treatment of other cutaneous conditions (in addition to hair), such as the treatment of leg veins, spider veins, angiomas, lesions, other vascular anomalies and other dermatological conditions affecting the skin of a patient.

Another advantage of the present invention is that it provides two or more pulsed lasers coupled by a sequence control device for emitting laser energy through a common optical delivery system which delivers simultaneous or sequential pulsed laser energy from the two or more pulsed lasers.

Another advantage of the present invention is that it provides an improved laser apparatus and method for adjusting pulse width and the time delay between pulses to customize treatment and the energy delivered to the spot being treated according to skin color, hair color, hair diameter and the anatomic site being treated.

Another advantage of the present invention is that it provides safe and permanent hair removal in a wider range of patients having hairs of all colors and skin of all colors, including patients with dark skin. Generally, the present invention will accommodate all persons having hair which is darker than their skin.

Another advantage of the present invention is that it provides a delay between laser pulses which is shorter than the thermal relaxation time of the hair being treated, so the hair does not cool off between pulses, and wherein the delay between laser pulses is longer than the thermal relaxation time of the skin, so the skin may dissipate heat and cool off between pulses and does not burn.

Another advantage of the present invention is that it provides a method and apparatus wherein the pulse width and delay between pulses may be varied to accommodate the thermal relaxation time of each patient's hair and skin.

Another advantage of the present invention is that it provides for an improved laser apparatus and method for treatment of other cutaneous conditions (in addition to hair) such as in the treatment of leg veins, spider veins, angiomas, lesions, other vascular anomalies and dermatological conditions effecting the skin of a patient.

Another advantage of the present invention is that it provides for an improved laser apparatus and method that is easy to use, and the laser apparatus is durable, light-weight and easily maintained.

Another advantage of the present invention is that it provides for an improved laser apparatus that provides a wider beam area (spot size on the skin) by utilizing two or more pulsed lasers coupled by a sequencer for delivering more laser energy to each spot allowing the spot size to be made larger for faster treatment.

A further advantage of the present invention is that it provides for an improved laser apparatus that is simple to manufacture and assemble in an economical manner, and is cost effective for the user.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. A laser apparatus for permanently removing a plurality of hair follicles from the skin of a patient, comprising:

a) at least first and second lasers for emitting at least first and second pulses of coherent light energy each having a pulse width in the range of ½ ms to 40 ms; being a parametrically defined pulse group;

b) optical delivery means connected to said at least first and second lasers for transmitting said at least first and second pulses of coherent light energy through a common optical pathway to the same spot on the skin of a patient for removing hair follicles;

c) means for controlling said at least first and second lasers to emit said at least first and second pulses of coherent light energy sequentially, with a time delay of less than 100 milliseconds between the sequential pulses from said at least first and second lasers; and d) a handpiece for holding a section of said common optical pathway for directing said at least first and second pulses of coherent light energy to a selected spot of the patient's skin to remove the plurality of hair follicles.

2. A laser apparatus in accordance with claim 1, wherein said means for controlling includes a sequencer device having a control module for controlling and modulating the sequential pulsing of each of said at least first and second lasers to sequentially emit said at least first and second pulses of coherent light energy, and for controlling the time delay to less than 10 ms between the sequential pulsing of said first and second lasers.

3. A laser apparatus in accordance with claim 2, wherein electronic timing device.

4. A laser apparatus in accordance with claim 2, further including an electrical panel box for supplying electrical power to said two or more lasers and to said sequencer device.

5. A laser apparatus in accordance with claim 1, wherein said optical delivery means includes at least two multi-strand fiber optic bundles for transmitting said at least first and second pulses of coherent light energy.

6. A laser apparatus in accordance with claim 5, wherein said at least two fiber optic bundles are combined to form a common fiber optic bundle for combining and transmitting said at least first and second pulses of coherent light energy to the same spot on the patient's skin.

7. A laser apparatus in accordance with claim 6, wherein said common fiber optic bundle is connected to said handpiece, said handpiece having a laser portal opening and lens for directing said at least first and second pulses of coherent light energy to the same spot on the patient's skin.

8. A laser apparatus in accordance with claim 1, wherein said handpiece includes a pulse firing button for sequentially pulsing said at least first and second lasers to sequentially emit said at least first and second pulses of coherent light energy for removing the plurality of hair follicles from the same spot on the skin of a patient.

9. A laser apparatus in accordance with claim 1, wherein said first and second lasers are different from each other.

10. A laser apparatus in accordance with claim 1, wherein said first and second lasers are the same as each other.

11. A laser apparatus in accordance with claim 9, wherein said first and second lasers includes one laser being an alexandrite laser and one laser being a ruby laser.

12. A laser apparatus in accordance with claim 9, wherein said first and second lasers includes one laser being an alexandrite laser and one laser being a diode laser.

13. A laser apparatus in accordance with claim 9, wherein said first and second lasers includes one laser being a diode laser and one laser being a ruby laser.

14. A laser apparatus in accordance with claim 10, wherein said first and second lasers includes two alexandrite lasers.

15. A laser apparatus in accordance with claim 10, wherein said first and second lasers includes two ruby lasers.

16. A laser apparatus in accordance with claim 10, wherein said first and second lasers includes two diode lasers.

17. A laser apparatus in accordance with claim 10, wherein said first and second lasers include two infrared lasers.

18. A laser apparatus in accordance with claim 9, wherein said first and second lasers include one laser being a diode laser and one laser being an infrared laser.

19. A laser apparatus in accordance with claim 1, further including a foot pedal switch assembly for initiating the sequential pulsing of said at least first and second lasers to sequentially emit said at least first and second pulses of coherent light energy for removing the plurality of hair follicles from the same spot of the skin of a patient.

20. A laser apparatus for permanently removing a plurality of hair follicles from the skin of a patient, comprising:

a) at least first and second lasers for emitting at least first and second pulses of coherent light energy each having a pulse width in the range of ½ ms to 40 ms; being a parametrically defined pulse group;

b) light transmission means connected to said at least first and second lasers for transmitting said at least first and second pulses of coherent light energy to the same spot on the skin of a patient through a common light transmission path for removing hair follicles;

c) means for controlling said at least first and second lasers to emit said at least first and second pulses of coherent light energy sequentially, with a time delay of less than 100 milliseconds between the sequential pulses from said at least first and second lasers; and d) a handpiece for holding a section of said common light transmission path for focusing said at least first and second pulses of coherent light energy on a selected spot of the patient's skin to remove the plurality of hair follicles.

21. A laser apparatus in accordance with claim 20, wherein said light transmission means includes at least two multi-strand fiber optic bundles for transmitting said at least first and second pulses of coherent light energy.

22. A laser apparatus in accordance with claim 20, wherein said light transmission means includes articulated arms having at least two movable sections with mirrors for transmitting said first and second sets of pulses of coherent light energy.

23. A laser apparatus in accordance with claim 22, wherein said articulated arms are connected to said handpiece, said handpiece having a laser portal opening for focusing said first and second sets of pulses of coherent light energy on the same spot of the patient's skin.

24. A laser apparatus in accordance with claim 20, wherein said means for controlling includes a sequencer device having a control module for controlling and modulating the sequential pulsing of said at least first and second lasers to sequentially emit said at least first and second pulses of coherent light energy, and for controlling the time delay to less than 100 ms between the sequential pulsing of said first and second lasers.

25. A laser apparatus in accordance with claim 24, wherein said control module is in the form of a microprocessor or an electronic timing device.

26. A laser apparatus in accordance with claim 24, further including an electrical panel box for supplying electrical power to said first and second lasers and to said sequencer device.

27. A laser apparatus in accordance with claim 20, wherein said handpiece includes a pulse firing button for initiating the sequential pulsing of said at least first and second lasers to sequentially emit said at least first and second pulses of light energy of coherent light energy for removing the plurality of hair follicles from the same spot of the skin of a patient.

28. A laser apparatus in accordance with claim 20, wherein said at least first and second lasers are different from each other.

29. A laser apparatus in accordance with claim 20, wherein said at least first and second lasers are the same as each other.

30. A laser apparatus in accordance with claim 28, wherein said at least first and second lasers includes one laser being an alexandrite laser and one laser being a ruby laser.

31. A laser apparatus in accordance with claim 28, wherein said at least two or more lasers includes one laser being an alexandrite laser and one laser being a diode laser.

32. A laser apparatus in accordance with claim 28, wherein said at least first and second lasers includes one laser being a diode laser and one laser being a ruby laser.

33. A laser apparatus in accordance with claim 29, wherein said at least first and second lasers includes two alexandrite lasers.

34. A laser apparatus in accordance with claim 29, wherein said at least first and second lasers includes two ruby lasers.

35. A laser apparatus in accordance with claim 29, wherein said at least first and second lasers includes two diode lasers.

36. A laser apparatus in accordance with claim 28, wherein said first and second lasers include two infrared lasers.

37. A laser apparatus in accordance with claim 28, wherein said first and second lasers include one laser being a diode laser and one laser being an infrared laser.

38. A laser apparatus in accordance with claim 20, further including a foot pedal switch assembly for initiating the sequential pulsing of said at least first and second lasers to sequentially emit said at least first and second pulses of coherent light energy for removing the plurality of hair follicles from the same spot of the skin of a patient.

39. A method of removing hair from the skin of a patient using a laser apparatus having at least first and second lasers, a sequence control device and an optical delivery system, comprising the steps of:

a) controlling said at least first and second lasers to sequentially emit at least first and second pulses of coherent light energy, respectively, each having a pulse width in the range of ½ ms to 40 ms;

b) transmitting said at least first and second pulses of coherent light energy to the same spot on the skin of the patient through a common light transmission pathway;

c) irradiating the same spot on the skin containing the hair with said at least first and second sequential pulses of coherent light energy transmitted through said common light transmission pathway from said at least first and second lasers;

d) pulsing said first laser at a wavelength in the range of 550 to 1200 nm, at a power level in the range of 5 to 80 Joules/cm$^2$, at a pulse duration in the range ½ to 40 milliseconds, having a pulse delay in the range of 5 to 100 milliseconds, and having a beam diameter on the treatment area in the range of 4 to 50 mm; and e) pulsing said second laser at a wavelength in the range of 550 to 1200 nm, at a power level in the range of 5 to 80 Joules/cM$^2$, at a pulse duration in the range of ½ to 40 milliseconds, having a pulse delay in the range of 5 to 100 milliseconds, and having a beam diameter on the treatment area in the range of 4 to 50 mm.

40. A method of removing hair from the skin of a patient using a laser apparatus having at least first and second lasers, a sequence control device and an optical delivery system, comprising the steps of:

a) controlling said at least first and second lasers to sequentially emit at least first and second pulses of coherent light energy, respectively, each having a pulse width in the range of ½ ms to 40 ms;

b) transmitting said at least first and second pulses of coherent light energy to the same spot on the skin of the patient through a common light transmission pathway;

c) irradiating the same spot on the skin containing the hair with said at least first and second sequential pulses of coherent light energy transmitted through said common light transmission pathway from said at least first and second lasers; and d) pulsing said first and second lasers to have a pulse delay between said first and second pulses less than the thermal relaxation time (TRT) of the patient's hair being treated to remove the patient's hair and in order to avoid burning of the patient's skin, said pulse delay between said first and second pulses being less than 100 ms.

* * * * *

UNITED STATES PATENT AND TRADEMARK OFFICE
CERTIFICATE OF CORRECTION

PATENT NO. : 6,149,645
DATED : November 21, 2000
INVENTOR(S) : Edward L. Tobinick It is certified that error appears in the above-identified patent and that said Letters Patent is hereby corrected as shown below:

Claim 3, line 1, after "wherein", insert --said control module is in the form of a microprocessor or an--.

Claim 22, second line, after "includes", insert --an--.

Claim 22, third line, change "arms" to --arm assembly--.

Claim 23, second line, change "arms are" to --arm assembly is--.

Signed and Sealed this

Twenty-ninth Day of May, 2001

*Attest:*

NICHOLAS P. GODICI

*Attesting Officer*     Acting Director of the United States Patent and Trademark Office